(12) United States Patent
Dall'Oglio et al.

(10) Patent No.: US 8,273,228 B2
(45) Date of Patent: Sep. 25, 2012

(54) PORTABLE DEVICE FOR THE MEASUREMENT AND CONTROL OF ANALYTES IN BIOLOGICAL FLUIDS

(75) Inventors: Giorgio Dall'Oglio, Milan (IT); Francesco Valgimigli, Florence (IT)

(73) Assignee: A. Menarini Industrie Farmaceutiche Riunite S.R.L., Florence (IT)

( * ) Notice: Subject to any disclaimer, the term of this patent is extended or adjusted under 35 U.S.C. 154(b) by 747 days.

(21) Appl. No.: 11/999,916

(22) Filed: Dec. 6, 2007

(65) Prior Publication Data

US 2008/0149478 A1     Jun. 26, 2008

(30) Foreign Application Priority Data

Dec. 7, 2006 (IT) ................. FI2006A0310

(51) Int. Cl.
*G01N 27/416* (2006.01)
*G01N 27/327* (2006.01)
(52) U.S. Cl. .................. 204/403.01; 600/345
(58) Field of Classification Search ........... 435/4–40.52, 435/287.1–288.7; 204/403.01–403.15, 518–545, 204/627–640; 205/777.5, 778, 792; 600/309–367
See application file for complete search history.

(56) References Cited

U.S. PATENT DOCUMENTS

| | | | |
|---|---|---|---|
| 4,266,021 A * | 5/1981 | Nylen et al. ............. | 435/14 |
| 4,832,034 A * | 5/1989 | Pizziconi et al. ......... | 600/366 |
| 5,791,344 A * | 8/1998 | Schulman et al. ........ | 600/347 |
| 6,171,238 B1 | 1/2001 | Klimes et al. | |
| 6,267,926 B1 * | 7/2001 | Reed et al. ............... | 422/48 |
| 6,618,603 B2 * | 9/2003 | Varalli et al. ............ | 600/345 |
| 2005/0177035 A1 * | 8/2005 | Botvinick et al. ........ | 600/347 |
| 2006/0222566 A1 | 10/2006 | Brauker et al. | |

FOREIGN PATENT DOCUMENTS

DE 44 05 149 A1 2/1994
EP 1 153 571 A1 11/2001

OTHER PUBLICATIONS

Office Action issued by the Patent Office of the Russian Federation on Jan. 27, 2012 regarding Application No. 2007145352.

* cited by examiner

*Primary Examiner* — Kaj K Olsen
*Assistant Examiner* — Susan D Leong
(74) *Attorney, Agent, or Firm* — Abelman, Frayne & Schwab

(57) ABSTRACT

Portable device for the measurement and control of analytes in biological fluids, provided with biosensor for measurement and control of biological fluids such as glucose and other analytes characterized by the possibility of using electrolytic cells with two, three or more electrodes, with polarization voltage between a few millivolts and 100 millivolts; the possibility of measuring the fluid temperature at the outlet of the electrolytic cell in high resolution mode for diagnostic purposes, hence it can also be used for performing very accurate thermal compensation of the electrochemical measurement; the possibility of performing optimised correction of both the systematic and random errors in the measurement performed; the possibility of calibrating the sensors used more accurately and efficiently and, lastly, the possibility of performing the measurement with much lower polarization voltages at the electrodes than the equipment in the state of the art with consequent benefits in terms of reduced wear of the electrodes used and reduced susceptibility to electrochemical interferences in the measuring phase.

11 Claims, 1 Drawing Sheet

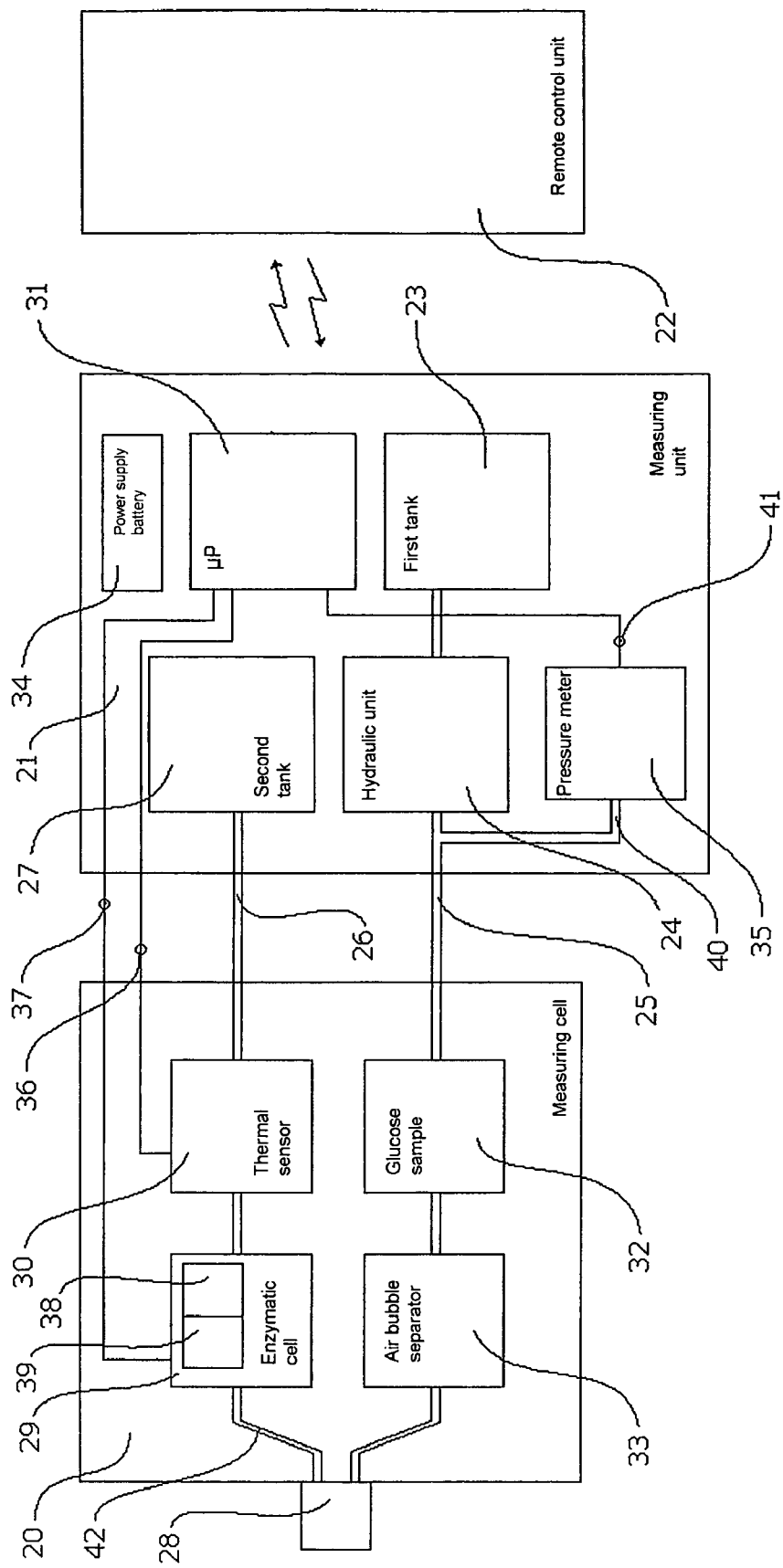

PORTABLE DEVICE FOR THE MEASUREMENT AND CONTROL OF ANALYTES IN BIOLOGICAL FLUIDS

FIELD OF THE INVENTION

The present invention refers to the field of devices for almost continuous extracellular biological fluid analysis lasting dozens of hours, and in particular the field of portable equipment provided with electrochemical biosensors for the measurement of glucose and other analytes.

STATE OF THE ART

In the medical field, the need for instruments suitable for monitoring the concentration of certain molecules in the blood of patients is well known. It is equally well known that from measurement of the quantity of said molecules in the extracellular liquids it is possible to identify, with an excellent degree of approximation, the corresponding hematic concentrations. This has stimulated the development of equipment and devices for measuring the concentration of analytes, for example glucose, in the extracellular liquids. Recently said equipment has been produced in a portable form, so as to further facilitate the use thereof, making it possible to use said equipment also in non-hospital environments.

The U.S. Pat. No. 5,791,344 concerns a portable device for the analysis of biological liquids which uses an electrochemical biosensor. This measuring instrument is powered by the mains and by battery only in the event of an emergency and not for operational service; this limit prevents the use thereof on patients who are free to move and in normal life mode. In addition to this limit, the "measuring cell" element described in the U.S. Pat. No. 5,791,344, which comprises the electrochemical transducer, requires the use of a battery inside the sensor with evident drawbacks in terms of maintenance and endurance. Furthermore the electrochemical transducer described in the U.S. Pat. No. 6,171,238 must be "wetted" in the manufacturing phase and kept in said state during the storage period, thus making this phase delicate and difficult to maintain efficient.

Other devices belonging to the state of the art, such as the one described in the German patent DE4405149 or in the European patent EP1153571 of the present applicant, use the technique via which the extracellular liquid sample containing glucose is collected by insertion of a microfibre for dialysis but entail the use of an enzymatic reaction cell inside the measuring instrument, and are therefore obliged to bring the sample to be measured to a constant pre-set temperature by means of a heater, with obvious complications in terms of control and management of the measurement. Lastly other devices, like the one described in the U.S. Pat. No. 6,171,238, permit the use of electrochemical transducers that are easier to manage, comprising a fixed part housed in the instrument and a movable and replaceable part, preferably of the disposable type, provided, for example, by a selective filtering membrane. The disadvantage of devices of this type is that the Clark-type sensor is designed for measurements on single samples of biological fluids, and as such is not specialised but allows the instrument to be adapted in order to perform many types of measurements. Consequently said instrument does not allow multiple measurements to be performed and neither does it provide the endurance of dozens of hours required of specialised measurement equipment for continuous measurements on individual patients.

In general, all the devices described in the above-listed documents specialising in the performance of continuous measurements on individual patients involve the use of electrochemical sensors provided with three or more electrodes operating with significant polarisation voltage which can reach values of over several hundred millivolts. The device described in the present patent application is able to operate with sensors provided with even only two electrodes, and with very low polarisation voltages, as little as only a few millivolts.

SUMMARY OF THE INVENTION

The present invention refers to a portable device provided with biosensor for measurement and control of biological fluids such as glucose and other analytes.

BRIEF DESCRIPTION OF THE DRAWINGS

FIG. 1 Block diagram of the portable device for the measurement and control of analytes in biological fluids according to the present invention.

DETAILED DISCLOSURE OF THE INVENTION

The present invention consists of a device for continuous measurement and control of analytes present in biological fluids which overcomes the drawbacks of the devices belonging to the state of the art by introducing numerous improvements: the possibility of using electrolytic cells with two, three or more electrodes, with polarisation voltage between a few millivolts and 100 millivolts; the possibility of measuring the fluid temperature at the outlet of said electrolytic cell in high resolution mode for diagnostic purposes, hence it can also be used for performing very accurate thermal compensation of the electrochemical measurement; the possibility of performing optimised correction of both the systematic and random errors in the measurement performed; the possibility of calibrating the sensors used more accurately and efficiently and, lastly, the possibility of performing the measurement with much lower polarisation voltages at the electrodes than the equipment in the state of the art with consequent benefits in terms of reduced wear of the electrodes used and reduced susceptibility to electrochemical interferences in the measuring phase.

FIG. 1 shows in detail the structure of the equipment according to the present invention. There are three separate modules:
- a disposable measuring cell 20;
- a measuring unit 21;
- a remote control unit 22;
- an electro-fluidic wiring 25, 26, 36, 37 which connects said disposable measuring cell 20 to said measuring unit 21.

Said measuring cell 20 comprises in turn:
- a subcutaneous probe 28;
- an enzymatic cell 29 combined with said subcutaneous probe 28 by means of an appropriate hydraulic connection 42;
- a thermal sensor 30 combined with a first capillary tube 26 at the outlet of said enzymatic cell 29 and forming part of said electro-fluidic wiring;
- an element containing a glucose sample 32 for functional verification of the system before insertion of the subcutaneous probe;
- an air bubble separator 33.

Said measuring unit 21, in turn, preferably comprises:
- a first tank 23 combined with a hydraulic unit 24 comprising pumping means suitable for conveying the solution contained in said first tank 23 into the subcutaneous area of the patient via the route comprising: a second capillary tube 25, forming part of said electro-fluidic wiring, entering the measuring cell 20; the element containing a glucose sample 32; the air bubble separator 33 and, lastly, the inlet tube of said subcutaneous probe 28;

a pressure meter 35 combined with said second capillary tube 25 by means of an appropriate hydraulic connection 40 and suitable for measuring the delivery pressure into said measuring cell 20;

a second tank 27 suitable for receiving said sample of interstitial liquid from said first capillary tube 26 after the measurement has been performed;

a control module 31 with microprocessor suitable for managing the sequence of measurement and recording operations performed by the device subject of the present invention and for managing the bidirectional communication of commands, measurements and programmes via radio towards the outside and in particular towards the remote control unit 22. Said microprocessor control module 31 will be connected to said thermal sensor 30 and to said enzymatic cell 29 by means of appropriate electrical connections 36, 37 forming part of said electro-fluidic wiring 25, 26, 36, 37 which connects said disposable measuring cell 20 to said measuring unit 21. Said microprocessor control module 31 will be further connected, by means of appropriate electrical connection 41, to said pressure meter 35 suitable for monitoring the delivery pressure into said measuring cell 20;

a power supply battery 34.

Said pumping means comprise a pump for example of the mechanical type—syringe or peristaltic—or a diaphragm or piezoelectric pump. Said air bubble separator 33 will preferably be provided with appropriate means for filtering and separating any micro air bubbles that could obstruct conveying of the solution contained in said first tank 23 into the subcutaneous area of the patient. In a preferred embodiment of the present invention said enzymatic cell 29 comprises in detail:

an enzymatic biosensor 38, of the two or three electrode type;

a reaction chamber 39 with an inlet and an outlet inside which said enzymatic biosensor 38 is housed.

As said previously, the device subject of the present invention can comprise enzymatic biosensors with three or two electrodes, thus offering extreme flexibility of use.

Operation of the device according to the present invention can be described as follows.

The measuring cell 20 is connected to the measuring 21 by means of an electro-fluidic wiring 25, 26, 36, 37 which connects the electrical terminals of the sensors 29 and 30 to the measuring circuit present in the module 31, and the solution delivery tubes 25 and collection tubes 26 to the tank 23 and to the discharge tank respectively. Before applying the measuring cell 20 to the patient, a functional test is performed on the enzymatic sensor, which can be activated by means of the remote control unit 22, after inserting the power supply battery 34 into the measuring unit 21. This Sensor Check procedure consists in pumping, with an appropriate flow, the perfusion solution through the element 32 containing a sample of glucose at known concentration, and in reading the consequent response of the enzymatic sensor acquiring the current signal for a period of a few minutes. An appropriate calculation algorithm determines whether the response falls within the predefined acceptance criteria. If the response is outside the above-mentioned criteria, the disposable measuring cell is replaced and the functional test is repeated. If the Sensor Check is positive, the measuring cell 20 is applied to the patient's skin after inserting the probe 28 under the skin by means of an appropriate guide needle, and the measuring unit 21 is strapped to the patient by means of an appropriate belt. At this point the monitoring is initiated by means of an appropriate command from the remote unit 22, which starts the pump, the measurement and recording of the data for dozens of hours. Via the remote unit 22 provided with appropriate display it is possible to connect at any time via radio to the recorder and display the measurements in real time in both numerical and graphic form. In particular the entire profile recorded up to that moment by the enzymatic sensor and by the temperature sensor can be displayed. The continuous temperature measurement is used to compensate the enzymatic sensor current and maximise accuracy of the measurement. This is accurate enough to continuously represent the actual body temperature of the patient with evident diagnostic value in addition to measurement of the glucose or other analyte detected by the enzymatic sensor. Said measuring cell 20 is provided with a device 33 for separation of any air bubbles present in the fluidic circuit which could affect measurement of the enzymatic sensor.

Said measurement cell 20 is provided with a device 33 for separation of any air bubbles present in the fluidic circuit which could affect measurement of the enzymatic sensor.

Said device 33 for separation of the air bubbles is produced by means of a chamber with two special membranes, one of which permits, at the working pressures, passage of the liquid along the fluidic line but separation of the bubbles, while the other permits outflow of the air accumulated in the chamber but not that of the perfusion liquid.

The invention claimed is:

1. Portable device for the measurement and control of analytes in biological fluids comprising: one disposable measuring cell suitable for application to the patient's skin, comprising in turn a subcutaneous probe, an enzymatic cell combined with said subcutaneous probe by means of an appropriate hydraulic connection, a thermal sensor combined with a first capillary tube at the outlet of said enzymatic cell and comprising an electro-fluidic wiring adapted to transmit fluids and electrical signals, an element containing a glucose sample for functional verification of the system before insertion of the subcutaneous probe, an air bubble separator; one measuring unit combined with said measuring cell and one remote control unit combined with said measuring cell and with said measuring unit and suitable for setting, adjusting and monitoring the measurement, wherein said disposable measuring cell is external to said measuring unit connected to said measuring unit by means of said electro-fluidic wiring and adapted to be placed attached to the subcutaneous probe and to the patient's skin.

2. Device as claimed in claim 1 wherein said measuring unit comprises: a first tank combined with a hydraulic unit; a pressure meter combined with a second capillary tube and suitable for assessing the delivery pressure into said measuring cell; a second tank suitable for receiving said sample of interstitial liquid from said second capillary tube after the measurement has been performed; a control module with microprocessor, suitable for managing the sequence of measuring and recording operations and the bidirectional communication of commands, measurements and programmes via radio towards the outside and in particular towards said remote control unit; a power supply battery.

3. Device as claimed in claim 1 wherein said hydraulic unit comprises pumping means suitable for conveying the solution contained in said first tank into the subcutaneous area of the patient through said measuring cell.

4. Device as claimed in claim 1 wherein said microprocessor control module is connected to said thermal sensor and to an enzymatic cell by means of appropriate electrical connections forming part of said electro-fluidic wiring and to a pressure meter by means of an appropriate electrical connection.

5. Device as claimed in claim 3 wherein said pumping means comprise a pump for example of the mechanical type—syringe or peristaltic—or a diaphragm or piezoelectric pump.

6. Device as claimed in claim 1 wherein said enzymatic cell comprises: a reaction chamber provided with an inlet and an outlet and in turn comprising inside an enzymatic biosensor.

7. Device as claimed in claim 6 wherein said enzymatic biosensor is of the three or two electrode type.

8. Device as claimed in claim 1 wherein said probe comprises an appropriate guide needle.

9. Device as claimed in claim 1 wherein said measuring unit is provided with appropriate means for anchoring to the patient's body.

10. Device as claimed in claim 1 wherein said remote unit comprises an appropriate display suitable for displaying the measurements performed in real time in both numerical and graphic form.

11. Device as claimed in claim 1 wherein said air bubble separation device is produced by means of a chamber with two special membranes one of which permits, at the working pressures, passage of the liquid along the fluidic line but separation of the bubbles, while the other permits outflow of the air accumulated in the chamber but not that of the perfusion liquid.

* * * * *